(12) United States Patent
Chang et al.

(10) Patent No.: US 11,530,948 B2
(45) Date of Patent: Dec. 20, 2022

(54) COMPACT RAMAN SENSOR AND APPARATUS FOR ESTIMATING BIO-COMPONENT

(71) Applicant: SAMSUNG ELECTRONICS CO., LTD., Suwon-si (KR)

(72) Inventors: Ho Jun Chang, Seoul (KR); Sung Hyun Nam, Yongin-si (KR); Alexey Anikanov, Suwon-si (KR); Yun S Park, Suwon-si (KR); Eui Seok Shin, Yongin-si (KR); Woochang Lee, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 290 days.

(21) Appl. No.: 16/914,679

(22) Filed: Jun. 29, 2020

(65) Prior Publication Data

US 2021/0181019 A1    Jun. 17, 2021

(30) Foreign Application Priority Data

Dec. 13, 2019   (KR) .................. 10-2019-0166984

(51) Int. Cl.
*G01N 21/00* (2006.01)
*G01J 3/02* (2006.01)
*A61B 5/145* (2006.01)
*A61B 5/1455* (2006.01)
*A61B 5/00* (2006.01)
*G01J 3/44* (2006.01)

(52) U.S. Cl.
CPC .......... *G01J 3/0256* (2013.01); *A61B 5/1455* (2013.01); *A61B 5/14532* (2013.01);
(Continued)

(58) Field of Classification Search
CPC ........ G01J 3/0256; G01J 3/021; G01J 3/0216; G01J 3/44; G01J 2003/104;
(Continued)

(56) References Cited

U.S. PATENT DOCUMENTS 6,503,478 B2    1/2003  Chaiken et al.
8,873,041 B1   10/2014  Chai et al.
(Continued)

FOREIGN PATENT DOCUMENTS

CN           108489962 A      9/2018
KR      1020130113136 A      10/2013
(Continued)

OTHER PUBLICATIONS

Choe, C., et al., "Depth profiles of hydrogen bound water molecule types and their relation to lipid and protein interaction in the human stratum corneum in vivo", Analyst, Issue 22, 2016, 2 pages.
(Continued)

*Primary Examiner* — Md M Rahman
(74) *Attorney, Agent, or Firm* — Sughrue Mion, PLLC

(57) ABSTRACT

A Raman sensor includes a light source assembly having a plurality of light sources configured to emit light to a plurality of skin points of skin, each of the plurality of skin points having a predetermined separation distance from a light collection region of the skin from which Raman scattered light is collected; a light collector configured to collect the Raman scattered light from the light collection region of the skin; and a detector configured to detect the collected Raman scattered light.

19 Claims, 13 Drawing Sheets

(52) U.S. Cl.
CPC .......... *A61B 5/14546* (2013.01); *A61B 5/443* (2013.01); *A61B 5/4872* (2013.01); *A61B 5/4875* (2013.01); *G01J 3/021* (2013.01); *G01J 3/0216* (2013.01); *G01J 3/44* (2013.01); *A61B 5/0075* (2013.01)

(58) Field of Classification Search
CPC ...... G01J 2003/106; G01J 3/0227; G01J 3/10; A61B 5/14532; A61B 5/14546; A61B 5/1455; A61B 5/443; A61B 5/4872; A61B 5/4875; A61B 5/0075; A61B 2562/0238; A61B 5/681; A61B 5/0064; G01N 2201/0221; G01N 21/65
USPC ....................................................... 356/73.1
See application file for complete search history.

(56) References Cited

U.S. PATENT DOCUMENTS

| | | | |
|---|---|---|---|
| 10,325,366 | B2 | 6/2019 | Mahadevan-Jansen et al. |
| 10,520,438 | B2 | 12/2019 | Kim et al. |
| 2008/0076985 | A1 | 3/2008 | Matousek et al. |
| 2010/0214562 | A1 | 8/2010 | Mahadevan-Jansen et al. |
| 2013/0090537 | A1 | 4/2013 | Schemmann et al. |
| 2014/0103224 | A1 | 4/2014 | Ng et al. |
| 2015/0051459 | A1 | 2/2015 | Van Duyne et al. |
| 2015/0164336 | A1 | 6/2015 | Mahadevan-Jansen et al. |
| 2018/0053298 | A1 | 2/2018 | Mahadevan-Jansen et al. |
| 2019/0246907 | A1 | 8/2019 | Vukelic et al. |
| 2019/0257761 | A1 | 8/2019 | Lee et al. |
| 2019/0277764 | A1 | 9/2019 | Chang et al. |

FOREIGN PATENT DOCUMENTS

| | | |
|---|---|---|
| KR | 1020190024510 A | 3/2019 |
| WO | 2017214604 A1 | 12/2017 |

OTHER PUBLICATIONS

Masson, L., et al., "Dual excitation wavelength system for combined fingerprint and high wavenumber Raman spectroscopy", Analyst, 2018, Issue 143, pp. 1-24.

Communication dated Feb. 12, 2021, from the European Patent Office in European Application No. 20191724.2.

COMPACT RAMAN SENSOR AND APPARATUS FOR ESTIMATING BIO-COMPONENT

CROSS-REFERENCE TO RELATED APPLICATION(S)

This application is based on and claims priority under 35 U.S.C. § 119 to Korean Patent Application No. 10-2019-0166984, filed on Dec. 13, 2019, in the Korean Intellectual Property Office, the disclosure of which is incorporated by reference herein in its entirety.

BACKGROUND

1. Field

The following description relates to a compact Raman sensor for measuring Raman scattered light from the skin, or a compact Raman sensor for measuring light having high light scattering due to turbidity, and technology for estimating a bio-component using the Raman sensor.

2. Description of Related Art

Raman spectroscopic analysis is a general method for qualitative and quantitative analysis of organic chemicals such as powder or liquid drugs. Recently, Raman spectroscopy has been applied to a wider range of samples including the measurement of living organisms. A non-invasive biometric sensor, which is based on spectroscopic analysis techniques such as Raman spectroscopic analysis, may non-invasively measure physical properties of samples such as skin components or blood components, thereby improving user convenience. However, when the non-invasive biometric sensor using Raman spectroscopic analysis is used for human bodies, laser power density is generally limited to permissible levels according to national or international standards for the safe use of lasers on human bodies. A representative example of such standards is the Maximum Permissible Exposure as defined by ANSI Z136.1-2014. A generally used Raman spectrometer is in the form of a microscope, and uses a total laser power of dozens of milliwatts (mWs) or more, which is condensed by using an object lens with high magnification, such that the laser power level exceeds the Maximum Permissible Exposure limit established in the ANSI Z136.1-2014 standard. Furthermore, the general Raman spectrometer has a large form factor, and thus has a low level of portability. Accordingly, there has been research on a compact Raman sensor for skin analysis, which provides similar performance compared to a large sensor even while meeting the Maximum Permissible Exposure limit, and which may be used more conveniently.

SUMMARY

Additional aspects will be set forth in part in the description which follows and, in part, will be apparent from the description, or may be learned by practice of the presented embodiments.

According to an aspect of an example embodiment, a Raman sensor may include a light source assembly having a plurality of light sources configured to emit light to a plurality of skin points of skin, each of the plurality of skin points having a predetermined separation distance from a light collection region of the skin from which Raman scattered light is collected; a light collector configured to collect the Raman scattered light from the light collection region of the skin; and a detector configured to detect the collected Raman scattered light.

The light source assembly may be configured to adjust a light intensity of each of the plurality of light sources to emit light within a maximum permissible exposure limit.

The predetermined separation distance may have a value greater than a sampling volume of the skin.

A center of the sampling volume may be located at a center of the light collector.

The predetermined separation distance may indicate a distance between a center of the light collection region of the skin, from which the Raman scattered light is collected, and a skin point on which the light is incident.

The plurality of light sources may be arranged on an outer periphery of the light collector in at least one of a linear shape, a circular shape, and a polygonal shape.

The light source assembly may include a reflection surface for reflecting the light, emitted by the plurality of light sources, toward the plurality of skin points.

The reflection surface may include a first reflection surface for reflecting the light, emitted by the plurality of light sources, in a predetermined direction; and a second reflection surface for reflecting the light, reflected by the first reflection surface, toward the plurality of skin points.

The predetermined direction may be a direction toward a center of the light collector.

The first reflection surface and the second reflection surface are formed in a concentric ring.

The predetermined separation distance is configured to be adjusted by a reflection angle of the second reflection surface.

The light source assembly may be configured to set all reflection angles of the second reflection surface to a same value, or adjust at least some of the reflection angles to a different value to set the predetermined separation distance to the same value for all of the plurality of skin points or to a different value for at least some of the plurality of skin points.

The light source assembly may include a filter for passing light of a specific wavelength, among the reflected light.

The second reflection surface may include a third reflection surface for reflecting a first light beam, reflected by the first reflection surface, toward a first skin point having a first predetermined separation distance; and a fourth reflection surface for reflecting a second light beam, reflected by the first reflection surface, toward a second skin point having a second predetermined separation distance.

The third reflection surface and the fourth reflection surface may be arranged in a concentric circle.

A radius of the third reflection surface and a radius of the fourth reflection surface may be different from each other.

The predetermined separation distance may be set based on at least one of a type of an analyte to be measured, a wavelength band, a light intensity, a shape of a device having the Raman sensor, a size of the device having the Raman sensor, and a computing performance of the device having the Raman sensor.

The light source assembly may include a filter for passing light of a specific wavelength, among the emitted light.

The plurality of light sources may include a first light source configured to emit first light of a first wavelength, and a second light source configured to emit second light of a second wavelength, wherein the light source assembly further comprises a reflection surface for reflecting the first light and the second light toward a first skin point having a first predetermined separation distance and a second skin point having a second predetermined separation distance.

The first light source and the second light source may be arranged in a concentric circle, and have different radiuses.

The reflection surface may include a first reflection surface for reflecting the first light and the second light in a predetermined direction; and a second reflection surface for reflecting the reflected first light toward the first skin point, and the reflected second light toward the second skin point.

The light source assembly further may include a filter for passing light of a first specific wavelength among the reflected first light, and passing light of a second specific wavelength among the reflected second light.

The light collector may include a lens for collimating the Raman scattered light from the skin; and a filter for removing light of a specific wavelength from the collimated Raman scattered light.

The light collector may include a light collecting shield which is positioned in a light collection path between the skin and the lens, and that is configured to prevent light, other than the Raman scattered light, from being collected.

According to an aspect of an example embodiment, an apparatus for estimating a bio-component may include a Raman sensor comprising a light source assembly having a plurality of light sources configured to emit light to a plurality of skin points having a predetermined separation distance from a light collection region of the skin from which Raman scattered light is collected, a light collector disposed at a center of the plurality of light sources and configured to collect the Raman scattered light from the light collection region of the skin, and a detector configured to detect the collected Raman scattered light; and a processor configured to control the Raman sensor, and to estimate a bio-component based on the Raman scattered light detected by the Raman sensor.

The light source assembly may include a reflection surface for reflecting the light, emitted by the plurality of light sources, toward the plurality of skin points having the predetermined separation distance.

The predetermined separation distance may have a value greater than a radius of a sampling volume, and wherein the processor is further configured to adjust the predetermined separation distance based on at least one of a type of a bio-component to be estimated, a shape of the apparatus for estimating the bio-component, and a computing performance of the apparatus for estimating the bio-component.

The processor may be configured to set all reflection angles of the reflection surface to the same value or adjust at least some of the reflection angles to a different value to set the predetermined distance to the same value for all of the plurality of skin points or to a different value for at least some of the skin points.

The bio-component may include at least one of blood glucose, cholesterol, triglyceride, protein, lipid, uric acid, moisture, collagen, keratin, and elastin.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
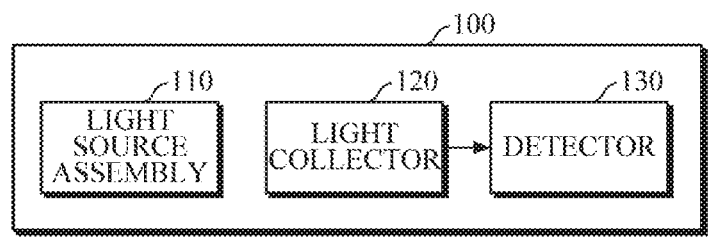
FIG. 1 is a block diagram illustrating an example of a compact Raman sensor according to an example embodiment.

Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

DETAILED DESCRIPTION

Hereinafter, embodiments of the present disclosure will be described in detail with reference to the accompanying drawings. It should be noted that wherever possible, the same reference symbols refer to the same elements, features, and structures, even in different drawings. In the following description, a detailed description of known functions and configurations incorporated herein may be omitted so as to not obscure the subject matter of the present disclosure.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to exemplary embodiments, and can be varied according to a purpose of a user or manager, or precedent and so on. Therefore, definitions of the terms should be made on the basis of the overall context.

It will be understood that, although the terms "first," "second," etc. may be used herein to describe various elements, these elements should not be limited by these terms. These terms are only used to distinguish one element from another. Any references to the singular form of a term may include the plural form of the term unless expressly stated otherwise. In the present specification, it should be understood that terms such as "including," "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated merely according to functions mainly performed by the components. That is, two or more components which will be described later can be integrated into a single component. Furthermore, a single component can be separated into two or more components. Moreover, each component can additionally perform some or all of a function executed by another component in addition to the main function thereof. Some or all of the main function of each component can be carried out by another component. Each component may be implemented in hardware, software, or a combination of both.

FIG. 1 is a block diagram illustrating an example of a compact Raman sensor.

Referring to FIG. 1, the compact Raman sensor 100 includes a light source assembly 110, a light collector 120, and a detector 130.

The light source assembly 110 may emit a plurality of light beams to a plurality of skin points having a predetermined source-detector separation (SDS). In this case, the predetermined SDS may be, for example, a value greater than an effective radius of a sampling volume of the skin. Here, the SDS may indicate a distance from a skin point, at which light emitted by the light source assembly 110 passes through a skin layer, to a skin point corresponding to a center position of the detector 130. Further, the light source assembly 110 may emit each of the plurality of light beams within maximum permissible exposure limits. In this case, the intensity of light, emitted by the light source assembly 110, may be configured to satisfy the maximum permissible exposure.

For example, if a maximum permissible exposure level is a (mW/mm$^2$), an effective radius of a sampling volume is b (mm), and four light beams are emitted to the skin, the light source assembly 110 may emit the four light beams to four skin points, having an SDS of c (mm) (b<c), with an intensity corresponding to a/4 (mW/mm$^2$). That is, the light source assembly 110 may emit a first light beam to a first skin point having an SDS of c (mm) (b<c) with an intensity corresponding to a/4 (mW/mm$^2$), may emit a second light beam to a second skin point having an SDS of c (mm) (b<c) with an intensity corresponding to a/4 (mW/mm$^2$), may emit a third light beam to a third skin point having an SDS of c (mm) (b<c) with an intensity corresponding to a/4 (mW/mm$^2$), and may emit a fourth light beam to a fourth skin point having an SDS of c (mm) (b<c) with an intensity corresponding to a/4 (mW/mm$^2$).

The light source assembly 110 may include a plurality of light sources. Each light source may emit light of a predetermined wavelength, such as visible light or infrared light, to the skin. However, the light source is not limited thereto, and wavelengths of light emitted by each light source may vary depending on the purpose of measurement or types of analytes. Further, each light source may be a single light-emitting body, or may be formed of an array of a plurality of light-emitting bodies. If each light source is formed of a plurality of light-emitting bodies, then the plurality of light-emitting bodies may emit light of the same wavelength or light of different wavelengths. Further, the plurality of light-emitting bodies may be classified into a plurality of groups, and each group of the light-emitting bodies may emit light of different wavelengths. For example, each light source may include a light-emitting diode (LED), a laser diode (e.g., a vertical cavity surface emitting laser (VCSEL), etc.), and the like, but this is merely an example and the light source is not limited thereto.

The light source assembly 110 may further include a filter (e.g., a long pass filter, a clean up filter, a bandpass filter, etc.) for passing light of a specific wavelength and/or an optical element (e.g., a reflection surface, etc.) for directing the emitted light toward a desired position of the skin.

The light collector 120 may collect Raman scattered light from the skin. The light collector 220 may include a filter (e.g., a long pass filter, a clean up filter, etc.), a lens (e.g., a collimating lens, a focusing lens, etc.), a fiber, a waveguide, and the like.

The detector 130 may detect the Raman scattered light collected by the light collector 120. For example, the detector 130 may include a photo diode, a photo transistor (PTr), an image sensor (e.g., a charge-coupled device (CCD), a complementary metal-oxide semiconductor (CMOS), etc.), and the like. The detector 130 may be a single device, or may be formed of an array of a plurality of devices. Further, the detector 130 may include a filter for detecting light of various wavelengths.

In the embodiments of the present disclosure, the SDS may be changed to various values based on at least one of a type of bio-information to be measured, a wavelength band, a light intensity, and the shape, size, and computing performance of a device having the Raman sensor. Accordingly, a physical size of the Raman sensor may be adjusted by reducing or changing a light path, and the Raman sensor may be manufactured in a compact size.

Figure 2:
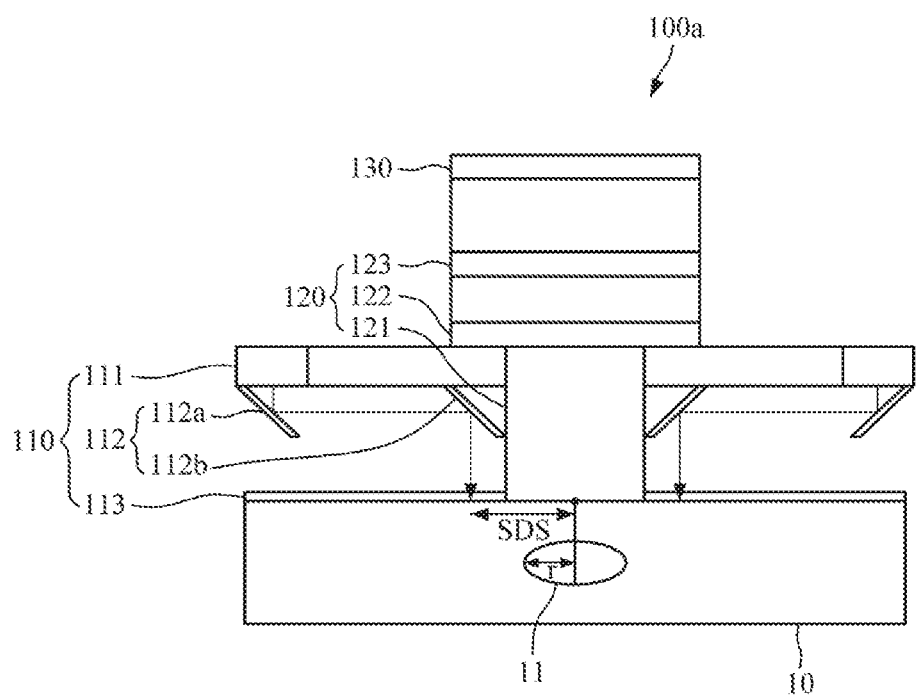
FIG. 2 is a diagram illustrating an example of a structure of a compact Raman sensor according to an example embodiment.
Figure 3:
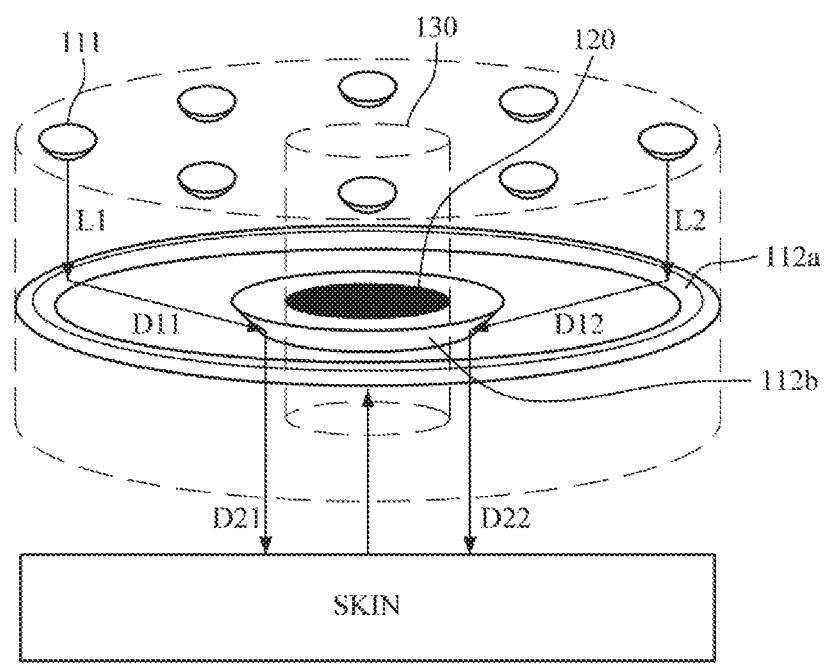
FIG. 3 is a diagram illustrating an example of an arrangement of light sources and reflection surfaces of the compact Raman sensor of FIG. 2 according to an example embodiment.

FIG. 2 is a diagram illustrating an example of a structure of a compact Raman sensor, and FIG. 3 is a diagram illustrating an example of an arrangement of light sources and reflection surfaces of the compact Raman sensor of FIG. 2. The compact Raman sensor 100*a* of FIGS. 2 and 3 may be an example of the compact Raman sensor 100 of FIG. 1. Although FIGS. 2 and 3 illustrate an example of eight light sources 111 and two reflection surfaces 112*a* and 112*b*, this is merely for convenience of explanation, and there is no limitation on the number of light sources and reflection surfaces.

Referring to FIGS. 2 and 3, the compact Raman sensor 100*a* includes the light source assembly 110, the light collector 120, and the detector 130.

The light source assembly 110 includes a plurality of light sources 111, a plurality of reflection surfaces 112, and a filter 113.

The plurality of light sources 111 may emit light of the same wavelength or light of different wavelengths. For example, all of the plurality of light sources 111 may emit light of the same wavelength or light of different wavelengths. Further, the plurality of light sources 111 may be classified into a plurality of groups, and each group of the light sources 111 may emit light of different wavelengths. In this case, the intensity of light, emitted by each of the plurality of light sources 111, may be assigned to satisfy the maximum permissible exposure.

For example, referring to FIG. 3, the plurality of light sources 111 may be arranged in a circle around the light collector 120 on an outer periphery of the light collector 120. However, this is merely an example, and there is no limitation on the arrangement of the light sources. For example, the plurality of light sources 111 may be arranged in various polygonal shapes such as a triangle, a square, a pentagon, and the like, or may be arranged in a linear shape based on the light collector 120, and the shape of the light sources 111 may be modified according to the shape of the Raman sensor.

The plurality of reflection surfaces 112 may reflect light emitted by the plurality of light sources 111, and direct the light toward a plurality of skin points. In this case, the plurality of skin points may be points having an SDS greater than an effective radius r of a sampling volume 11 of skin 10. The plurality of reflection surfaces 112 may be mirrors, but are not limited thereto, and may be objects which are surface-treated with various materials to have high reflectivity at a laser wavelength.

The plurality of reflection surfaces 112 may include a first reflection surface 112a and a second reflection surface 112b.

The first reflection surface 112a may reflect light beams L1 and L2 emitted by the plurality of light sources 111 in first directions D11 and D12. In this case, the first directions may be directions toward the center of the detector 130.

The second reflection surface 112b may reflect the light beams, reflected by the first reflection surface 112a, in second directions D21 and D22. In this case, the second directions may be directions toward skin points near the sampling volume 11, at which an SDS is greater than the effective radius r of the sampling volume 11 of the skin 10.

The first reflection surface 112a and the second reflection surface 112b may be arranged in a concentric ring around the light collector 120, as illustrated in FIG. 3. In this case, a radius of the first reflection surface 112a may be greater than a radius of the second reflection surface 112b. However, the first reflection surface 112a and/or the second reflection surface 112b may be formed in other shapes than as shown in FIG. 3, and may be formed as separate surfaces corresponding to each light source.

Although FIG. 3 illustrates an example in which the first reflection surface 112a and the second reflection surface 112b are formed at the same angle, the first reflection surface 112a and the second reflection surface 112b may be formed at different angles. For example, at least a partial or entire second reflection surface 112b may be formed at a different reflection angle. For example, a reflection angle of the second reflection surface 112b for reflecting the light beam L1, emitted by the first light source 111, in the second direction D21 may be set differently from a reflection angle of the second reflection surface 112b for reflecting the light beam L2, emitted by the second light source 111, in the second direction D22. As described above, by adjusting the reflection angle of the second reflection surface 112b, all the light beams emitted by the plurality of light sources 111 may be incident on skin points that each have the same SDS, or may be incident on skin points that have at least some different SDS values.

The filter 113 may pass light of a specific wavelength, among the light beams reflected from the second reflection surface 112b. For example, the filter 113 may be a long pass filter, a clean up filter, a bandpass filter, and the like.

The filter 113 may have holes formed at the center thereof, so as to allow the light collector 120 to collect Raman scattered light from the skin 10.

The light collector 120 may be disposed at the center of the compact Raman sensor 100a, to collect Raman scattered light from the skin 10. The light collector 120 may include a light collecting shield 121, a lens 122, and a filter 123.

The light collecting shield 121 is positioned in a light collection path between the skin 10 and the lens 122, to prevent light other than the Raman scattered light, such as diffused light, from being collected.

The lens 122 may collimate the Raman scattered light having passed through the light collecting shield 121. For example, the lens 122 may be a collimating lens.

The filter 123 may remove light of a specific wavelength from the collimated Raman scattered light. For example, the filter 123 may be a rejection filter such as a notch filter, a long-pass filter, and the like.

The detector 130 may detect the Raman scattered light having passed through the filter 123. For example, the detector 130 may include a photo diode, a PTr, an image sensor (e.g., a CCD, a CMOS, etc.), and the like.

The number and positions of the light sources 111, and the positions and angles of the first reflection surface 112a and the second reflection surface 112b are not limited to the examples illustrated in FIGS. 2 and 3, and may be set and changed to various values according to the purpose of measurement, an analyte, a device size, a desired SDS value, and the like.

Figure 4:
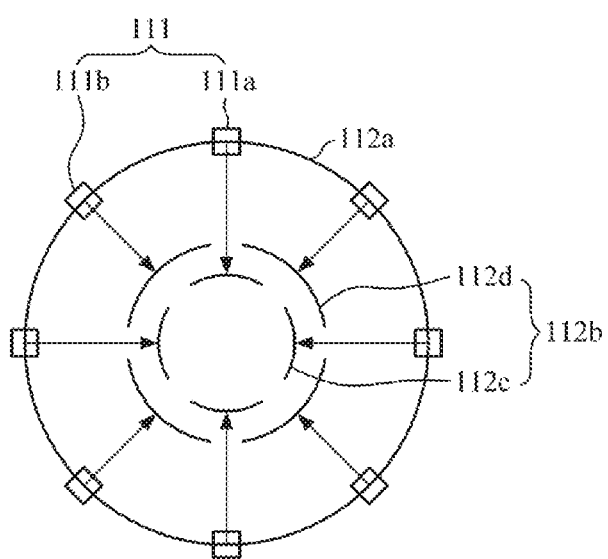
FIG. 4 is a diagram illustrating another example of an arrangement of light sources and reflection surfaces of the compact Raman sensor of FIG. 2 according to an example embodiment.

FIG. 4 is a is a plan view schematically illustrating another example of an arrangement of light sources and reflection surfaces of the compact Raman sensor of FIG. 2. Although FIG. 4 illustrates an example of eight light sources 111 and nine reflection surfaces 112a, 112c, and 112d, this is merely for convenience of explanation, and there is no limitation on the number of light sources 111 and reflection surfaces 112.

Referring to FIGS. 2 and 4, the plurality of light sources 111 may be divided into a first group and a second group according to wavelengths of the emitted light. A plurality of light sources 111a, included in the first group, may emit a first light beam of a first wavelength, and a plurality of light sources 111b, included in the second group, may emit a second light beam of a second wavelength. In this case, the first wavelength and the second wavelength may be different from each other.

The reflection surface 112 includes the first reflection surface 112a and the second reflection surface 112b, and the second reflection surface 112b includes a plurality of third reflection surfaces 112c and a plurality of fourth reflection surfaces 112d.

The third reflection surfaces 112c may reflect the first light beam, reflected by the first reflection surface 112a, toward a first skin point having a first SDS, and the fourth reflection surfaces 112d may reflect the second light beam, reflected by the first reflection surface 112a, toward a second skin point having a second SDS. In this case, the first SDS and the second SDS may be different values, and the first SDS may be, for example, a value smaller than the second SDS. The third reflection surfaces 112c and the fourth reflection surfaces 112d may be arranged in a concentric circle around the light collector 120, but are not limited thereto. In this case, a radius of the fourth reflection surface 112d may be greater than a radius of the third reflection surface 112c.

In the embodiments of the present disclosure, by arranging the reflection surfaces 112 in a plurality of circles having different radiuses, two-dimensional Raman images may be obtained according to various SDS values. Further, by using a plurality of light sources 111 which emit light of different wavelengths, two-dimensional Raman images may be obtained for various wavelengths. However, the Raman image is not limited thereto, and may also be obtained by using only one wavelength according to a type of an analyte and a signal band, and using different SDS values as illustrated in FIG. 4. For example, moisture in a high wavelength region may be measured by using laser at a single wavelength of 660 nanometers (nm) or 675 nm and by analyzing a Raman scattered image according to two or more different SDS values. As described above, by analyzing the Raman image for a short SDS and the Raman image for a long SDS, a difference in moisture content between a portion located near the skin surface and a portion located relatively more inside the skin surface may be analyzed.

Figure 5:
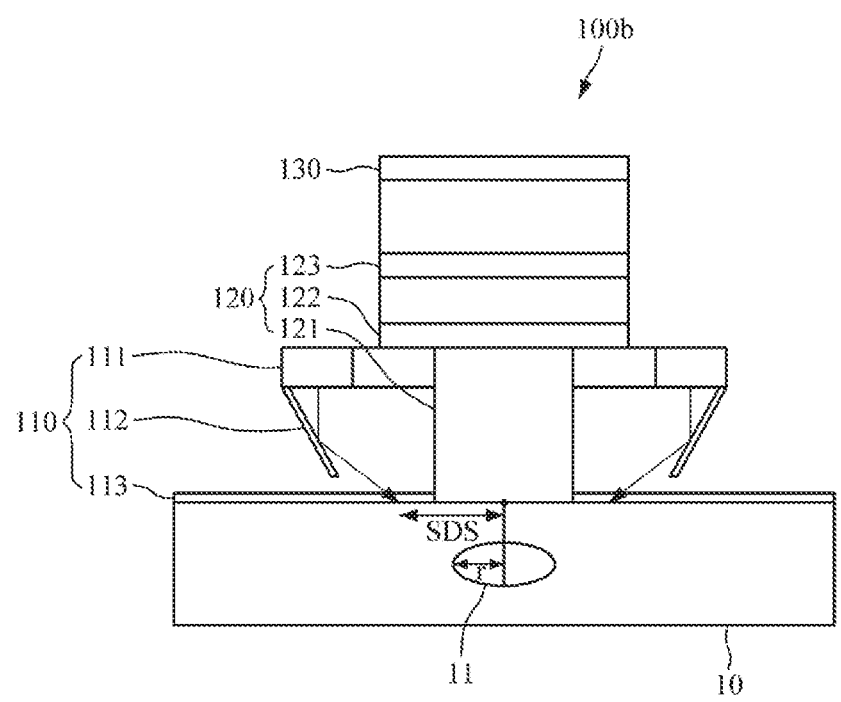
FIG. 5 is a diagram illustrating another example of a structure of a compact Raman sensor according to an example embodiment.
Figure 6:
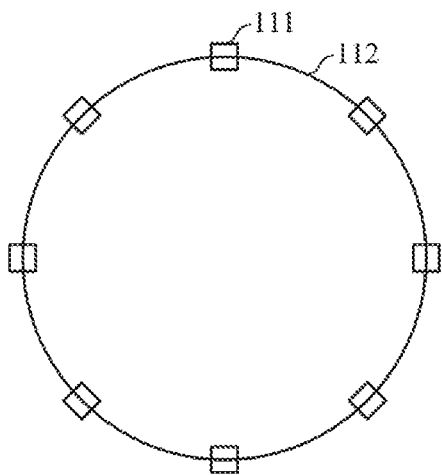
FIG. 6 is a diagram illustrating an example of an arrangement of light sources and reflection surfaces of the compact Raman sensor of FIG. 5 according to an example embodiment.

FIG. 5 is a diagram illustrating another example of a structure of a compact Raman sensor, and FIG. 6 is a diagram illustrating an example of an arrangement of light sources and reflection surfaces of the compact Raman sensor of FIG. 5. The compact Raman sensor 100b of FIGS. 5 and 6 may be an example of the compact Raman sensor 100 of FIG. 1. Although FIGS. 5 and 6 illustrate an example of eight light sources 111 and one reflection surface 112, this is merely for convenience of explanation, and there is no limitation on the number of light sources and reflection surfaces.

Referring to FIGS. 5 and 6, the compact Raman sensor 100b includes the light source assembly 110, the light collector 120, and the detector 130.

The light source assembly 110 includes a plurality of light sources 111, a reflection surface 112, and a filter 113.

The plurality of light sources 111 may emit light of the same wavelength or light of different wavelengths. For example, all the plurality of light sources 111 may emit light of the same wavelength or light of different wavelengths. Further, the plurality of light sources 111 may be classified into a plurality of groups, and each group of the light sources 111 may emit light of different wavelengths. In this case, the intensity of light, emitted by each of the plurality of light sources 111, may be assigned to the plurality of light sources 111 to satisfy the maximum permissible exposure.

The plurality of light sources 111 may be arranged in a circle around the light collector 120 on an outer periphery of the light collector 120. However, this is merely an example, and the shape thereof may be modified to various shapes such as a linear shape, a polygonal shape, and the like.

The reflection surface 112 may reflect light beams, emitted by the plurality of light sources 111, to a plurality of skin points each having an SDS greater than the effective radius r of the sampling volume 11 of the skin 10. The reflection surface 112 may be formed in a ring shape around the light collector 120, but is not limited to the ring shape, and may be formed as separate surfaces corresponding to each of the plurality of light sources 111.

The filter 113 may pass light of a specific wavelength, among the lights reflected by the reflection surface 112. For example, the filter 113 may be a long pass filter, a clean up filter, a bandpass filter, and the like.

The filter 113 may have holes formed at the center thereof, so as to allow the light collector 120 to collect Raman scattered light from the skin 10.

The light collector 120 may be disposed at the center of the compact Raman sensor 100b, to collect Raman scattered light from the skin 10. The light collector 120 may include a light collecting shield 121, a lens 122, and a filter 123.

The light collecting shield 121 is positioned in a light collection path between the skin 10 and the lens 122, to prevent light other than the Raman scattered light, such as diffused light, from being collected.

The lens 122 may collimate the Raman scattered light having passed through the light collecting shield 121. For example, the lens 122 may be a collimating lens.

The filter 123 may remove light of a specific wavelength from the collimated Raman scattered light. For example, the filter 123 may be a rejection filter such as a notch filter, a long-pass filter, and the like.

The detector 130 may detect the Raman scattered light having passed through the filter 123. For example, the detector 130 may include a photo diode, a PTr, an image sensor (e.g., a CCD, a CMOS, etc.), and the like.

The number and positions of the light sources 111, and the position and angle of the reflection surface 112 are not limited to the examples illustrated in FIGS. 5 and 6, and may be set and changed to various values according to the purpose of measurement, an analyte, a device size, a desired SDS value, and the like.

Figure 7:
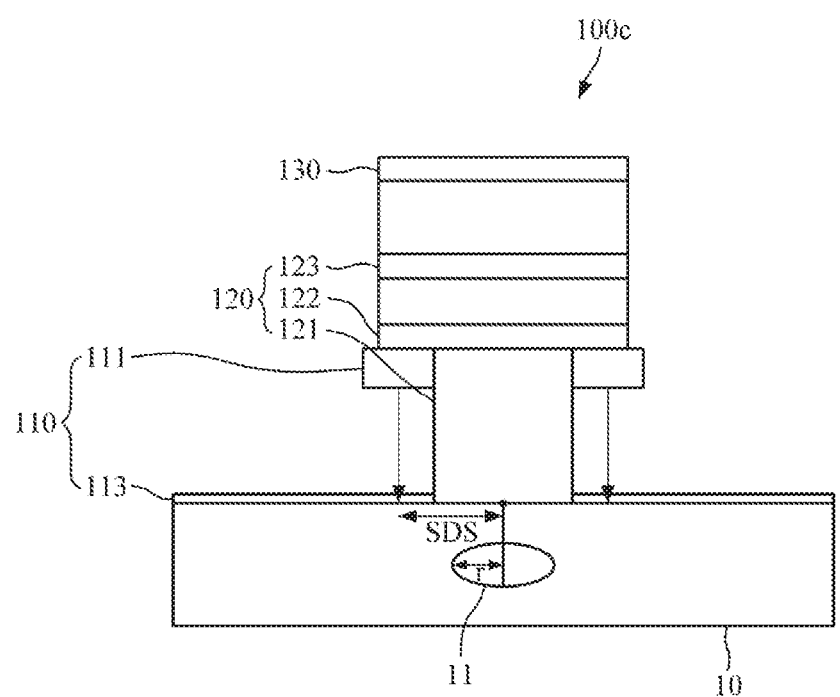
FIG. 7 is a diagram illustrating yet another example of a structure of a compact Raman sensor according to an example embodiment.

FIG. 7 is a diagram illustrating yet another example of a structure of a compact Raman sensor. The compact Raman sensor 100c of FIG. 7 may be an example of the compact Raman sensor 100 of FIG. 1.

Referring to FIG. 7, the compact Raman sensor 100c includes the light source assembly 110, the light collector 120, and the detector 130.

The light source assembly 110 includes a plurality of light sources 111 and a filter 113.

The plurality of light sources 111 may emit light of the same wavelength or light of different wavelengths to a plurality of skin points having an SDS greater than the effective radius r of the sampling volume 11 of the skin 10. For example, each of the plurality of light sources 111 may emit light of the same wavelength or light of different wavelengths. Further, the plurality of light sources 111 may be classified into a plurality of groups, and each group of the light sources 111 may emit light of different wavelengths. In this case, the intensity of light, emitted by each of the plurality of light sources 111, may be assigned to the plurality of light sources 111 to meet the maximum permissible exposure.

As illustrated in FIGS. 3, 4, and 6, the plurality of light sources 111 may be arranged in a circle around the light collector 120 on an outer periphery of the light collector 120. However, the shape of the light sources 111 is not limited thereto as described above.

The filter 113 may pass light of a specific wavelength, among the lights emitted by the plurality of light sources 111. In this case, the filter 113 may be a long pass filter, a clean up filter, a bandpass filter, and the like, but is not limited thereto.

The filter 113 may have holes formed at the center thereof, so as to allow the light collector 120 to collect Raman scattered light from the skin 10.

The light collector 120 may be disposed at the center of the compact Raman sensor 100c, to collect Raman scattered light from the skin 10. The light collector 120 may include a light collecting shield 121, a lens 122, and a filter 123.

The light collecting shield 121 is positioned in a light collection path between the skin 10 and the lens 122, to prevent light other than the Raman scattered light, e.g., diffused light, from being collected.

The lens 122 may collimate the Raman scattered light having passed through the light collecting shield 121. For example, the lens 122 may be a collimating lens.

The filter 123 may remove light of a specific wavelength from the collimated Raman scattered light. For example, the filter 123 may be a rejection filter such as a notch filter, a long-pass filter, and the like.

The detector 130 may detect the Raman scattered light having passed through the filter 123. For example, the detector 130 may include a photo diode, a PTr, an image sensor (e.g., a CCD, a CMOS, etc.), and the like.

The number and positions of the light sources 111 are not limited to the example illustrated in FIG. 7, and may be set and changed to various values according to the purpose of measurement, an analyte, a device size, a desired SDS value, and the like.

Figure 8:
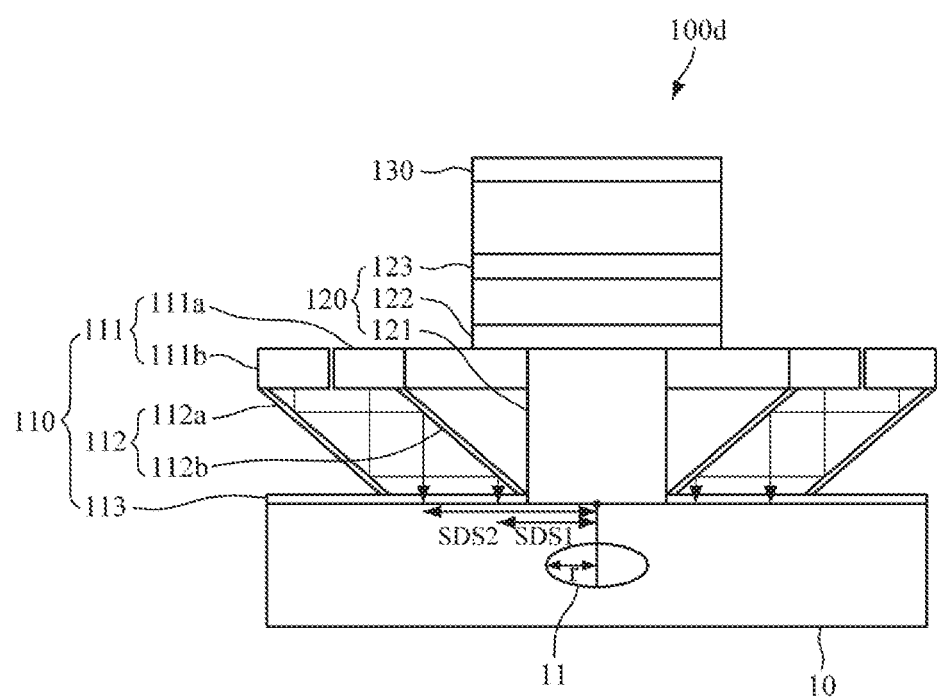
FIG. 8 is a diagram illustrating still another example of a structure of a compact Raman sensor according to an example embodiment.
Figure 9:
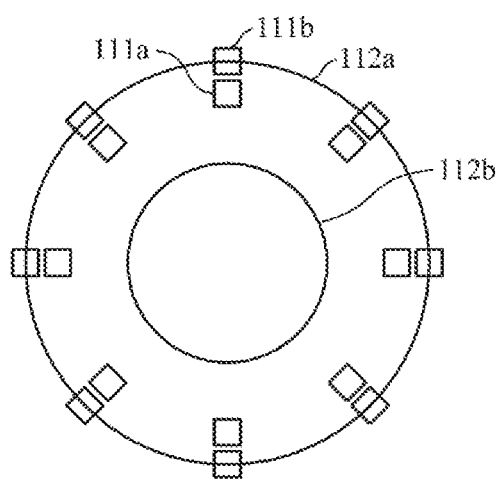
FIG. 9 is a diagram illustrating an example of an arrangement of light sources and reflection surfaces of the compact Raman sensor of FIG. 8 according to an example embodiment.

FIG. 8 is a diagram illustrating still another example of a structure of a compact Raman sensor, and FIG. 9 is a diagram illustrating an example of an arrangement of light sources and reflection surfaces of the compact Raman sensor of FIG. 8. The compact Raman sensor 100d of FIGS. 8 and 9 may be an example of the compact Raman sensor 100 of FIG. 1. FIGS. 8 and 9 illustrate an example of sixteen light sources 111a and 111b and two reflection surfaces 112a and 112b, in which the sixteen light sources 111a and 111b are divided into two groups. However, this is merely for convenience of explanation, and there is no limitation on the number of light sources, reflection surfaces, and groups.

Referring to FIGS. 8 and 9, the compact Raman sensor 100d includes the light source assembly 110, the light collector 120, and the detector 130.

The light source assembly 110 includes a plurality of light sources 111, a plurality of reflection surfaces 112, and a filter 113.

The plurality of light sources 111 may be divided into two groups according to the position of the light sources 111 and/or wavelengths of the emitted light. A plurality of first light sources 111a, included in a first group, may emit light of a first wavelength, and a plurality of second light sources 111b, included in a second group, may emit light of a second wavelength. In this case, the first wavelength and the second wavelength may be different from each other, and the intensity of light, emitted by each of the plurality of light sources 111, may be assigned to the plurality of light sources 111 to satisfy the maximum permissible exposure.

The plurality of first light sources 111a, included in the first group, may be arranged in a circle around the light collector 120 on an outer periphery of the light collector 120, and the plurality of second light sources 111b, included in the second group, may be arranged in a circle on an outer periphery of the plurality of first light sources 111a. The plurality of first light sources 111a included in the first group and the plurality of second light sources 111b included in the second group may be arranged in a concentric circle. However, the arrangement of the light sources is merely an example, and may be modified in various shapes according to an analyte to be measured and the like.

The plurality of reflection surfaces 112 may reflect light, emitted by the plurality of light sources 111, toward a plurality of skin points having an SDS greater than the effective radius r of the sampling volume 11 of the skin 10. The plurality of reflection surfaces 112 may include a first reflection surface 112a and a second reflection surface 112b.

The first reflection surface 112a may reflect light beams of the first wavelength, emitted by the plurality of first light sources 111a, in a first direction, and may reflect light beams of the second wavelength, emitted by the plurality of second light sources 111b, in the first direction. In this case, the first direction may be a direction toward the center of the detector 130.

The second reflection surface 112b may reflect the light beams of the first wavelength, reflected by the first reflection surface 112a, in a second direction, and may reflect the light beams of the second wavelength, reflected by the first reflection surface 112a, in a third direction. In this case, the second direction may be a direction of a skin point having a first SDS, and the third direction may be a direction of a skin point having a second SDS. In this case, the first SDS and the second SDS may be different values, and may be values greater than the effective radius r of the sampling volume 11 of the skin 10.

The first reflection surface 112a and the second reflection surface 112b may be arranged in a concentric ring around the light collector 120. In this case, a radius of the first reflection surface 112a may be greater than a radius of the second reflection surface 112b. However, the first reflection surface 112a and the second reflection surface 112b are not limited thereto.

The filter 113 may pass light of a specific wavelength, among the lights reflected by the second reflection surface 112b. In one embodiment, the filter 113 may be a long pass filter, a clean up filter, a bandpass filter, and the like.

In one embodiment, the filter 113 may have holes formed at the center thereof, so as to allow the light collector 120 to collect Raman scattered light from the skin 10.

The light collector 120 may be disposed at the center of the compact Raman sensor 100d, to collect Raman scattered light from the skin 10. The light collector 120 may include a light collecting shield 121, a lens 122, and a filter 123.

The light collecting shield 121 is positioned in a light collection path between the skin 10 and the lens 122, to prevent light other than the Raman scattered light, such as diffused light, from being collected.

The lens 122 may collimate the Raman scattered light having passed through the light collecting shield 121. For example, the lens 122 may be a collimating lens.

The filter 123 may remove light of a specific wavelength from the collimated Raman scattered light. For example, the filter 123 may be a rejection filter such as a notch filter, a long-pass filter, and the like.

The detector 130 may detect the Raman scattered light having passed through the filter 123. In one embodiment, the detector 130 may include a photo diode, a PTr, an image sensor (e.g., a CCD, a CMOS, etc.), and the like.

The number and positions of the light sources 111, and the positions and angles of the first reflection surface 112a and the second reflection surface 112b are not limited to the examples illustrated in FIGS. 8 and 9, and may be set and changed to various values according to the purpose of measurement, an analyte, a device size, a desired SDS value, and the like.

Figure 10:
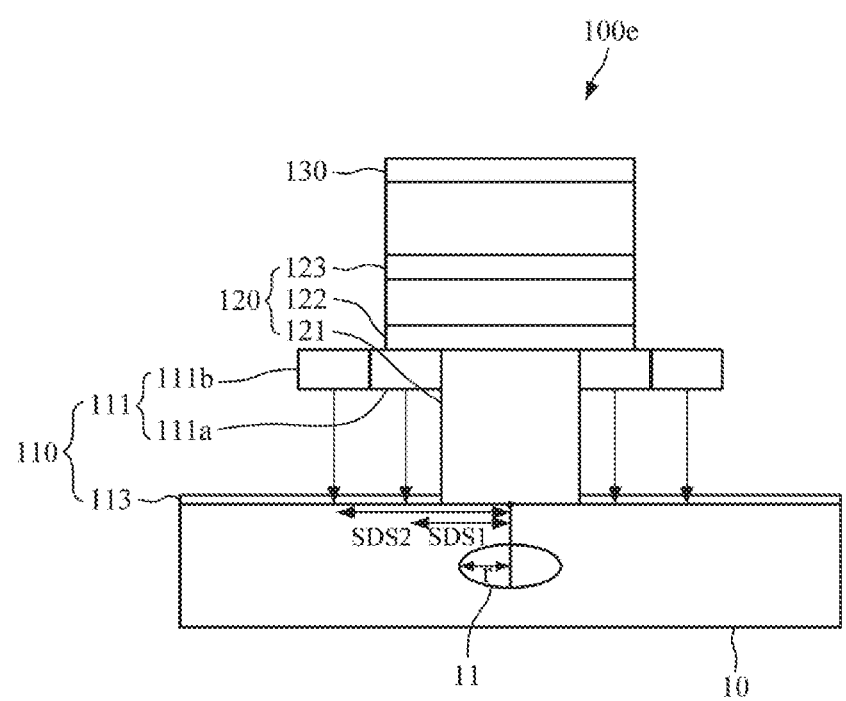
FIG. 10 is a diagram illustrating still another example of a structure of a compact Raman sensor according to an example embodiment.

FIG. 10 is a diagram illustrating still another example of a structure of a compact Raman sensor. The compact Raman sensor 100e of FIG. 10 may be an example of the compact Raman sensor 100 of FIG. 1.

Referring to FIG. 10, the compact Raman sensor 100e includes the light source assembly 110, the light collector 120, and the detector 130.

The light source assembly 110 includes a plurality of light sources 111 and a filter 113.

The plurality of light sources 111 may be divided into two groups according to the position of the light sources 111 and/or wavelengths of the emitted light. A plurality of light sources 111a, included in a first group, may emit light of a first wavelength to a plurality of skin points having a first SDS, and a plurality of light sources 111b, included in a second group, may emit light of a second wavelength to a plurality of skin points having a second SDS. In this case, the first wavelength and the second wavelength may be different from each other, and the intensity of light, emitted by each of the plurality of light sources 111, may be assigned to the plurality of light sources 111 to satisfy the maximum permissible exposure. Further, the first SDS and the second SDS may be values greater than the effective radius r of the sampling volume 11 of the skin 10.

For example, as illustrated in FIG. 10, the plurality of light sources 111a, included in the first group, may be arranged in a circle around the light collector 120 on an outer periphery of the light collector 120, and the plurality of light sources 111b, included in the second group, may be arranged in a circle on an outer periphery of the plurality of light sources 111a included in the first group. In this case, the plurality of light sources 111a included in the first group and the plurality of light sources 111b included in the second group may be arranged in a concentric circle or in a polygonal shape. As described above, by providing the plurality of light sources which are arranged to emit light to two or more skin points having different SDS values, reflection surfaces may be omitted, and the Raman sensor may be manufactured in a compact size.

The filter 113 may pass light of a specific wavelength, among the lights emitted by the plurality of light sources 111. In one embodiment, the filter 113 may be a long pass filter, a clean up filter, a bandpass filter, and the like.

The filter 113 may have holes formed at the center thereof, so as to allow the light collector 120 to collect Raman scattered light from the skin 10.

The light collector 120 may be disposed at the center of the compact Raman sensor 100e, to collect Raman scattered light from the skin 10. The light collector 120 may include a light collecting shield 121, a lens 122, and a filter 123.

The light collecting shield 121 is positioned in a light collection path between the skin 10 and the lens 122, to prevent light other than the Raman scattered light, such as diffused light, from being collected.

The lens 122 may collimate the Raman scattered light having passed through the light collecting shield 121. For example, the lens 122 may be a collimating lens.

The filter 123 may remove light of a specific wavelength from the collimated Raman scattered light. For example, the filter 123 may be a rejection filter such as a notch filter, a long-pass filter, and the like.

The detector 130 may detect the Raman scattered light having passed through the filter 123. In one embodiment, the detector 130 may include a photo diode, a PTr, an image sensor (e.g., a CCD, a CMOS, etc.), and the like.

The number and positions of the light sources 111 are not limited to the example illustrated in FIG. 10, and may be set and changed to various values according to the purpose of measurement, an analyte, a device size, a desired SDS value, and the like.

In the above descriptions of FIGS. 1 to 10, the light sources 111 and the reflection surfaces 112 are fixed, but are not limited thereto. That is, the light sources 111 and/or the reflection surfaces 112 may move or rotate according to a predetermined control signal, and Raman scattered light may be detected for various SDS values by the movement or rotation of the light sources 111 and/or the reflection surfaces 112.

Figure 11:
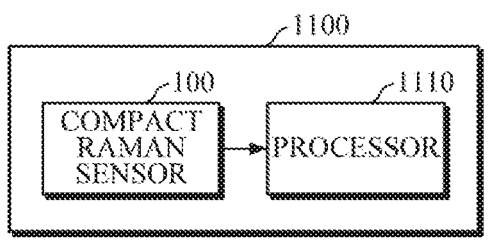
FIG. 11 is a diagram illustrating an example of an apparatus for estimating a bio-component according to an example embodiment.

FIG. 11 is a diagram illustrating an example of an apparatus for estimating a bio-component.

The apparatus 1100 for estimating a bio-component may be embedded in an electronic device or may be enclosed in a housing to be provided as a separate device. In this case, examples of the electronic device may include a cellular phone, a smartphone, a tablet personal computer (PC), a laptop computer, a personal digital assistant (PDA), a portable multimedia player (PMP), a navigation device, an MP3 player, a digital camera, a wearable device, and the like; and examples of the wearable device may include a wristwatch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited to the above examples, and the wearable device is neither limited thereto.

Referring to FIG. 11, the apparatus 1100 for estimating a bio-component includes the compact Raman sensor 100 and a processor 1110. The compact Raman sensor 100 is described above with reference to FIGS. 1 to 10, such that detailed description thereof will be omitted.

The processor 1110 may control the overall operation of the apparatus 1100 for estimating a bio-component, and may process various signals associated with the operation of the apparatus 1100 for estimating a bio-component.

The processor 1110 may drive each light source of the compact Raman sensor 100 sequentially or simultaneously according to a predetermined control signal. In this case, the processor 1110 may drive each light source of the compact Raman sensor 100 by referring to predetermined light source driving conditions. In this case, the light source driving conditions may include an emission time, a driving sequence, a current intensity, a pulse duration, and the like, of each light source.

The processor 1110 may obtain a two-dimensional Raman image of the skin based on Raman scattered light detected by the compact Raman sensor 100. When a light source and/or a reflection surface of the compact Raman sensor 100 are capable of moving or rotating, the processor 1110 may obtain the two-dimensional Raman image for various SDS values by moving or rotating the light source and/or the reflection surface according to a predetermined control signal.

The processor 1110 may estimate a bio-component of an object by analyzing the obtained two-dimensional Raman image. Here, the bio-component may include blood components such as blood glucose, cholesterol, triglyceride, protein, lipid, uric acid, etc., and components in the skin such as moisture, collagen, keratin, elastin, etc.

Figure 12:
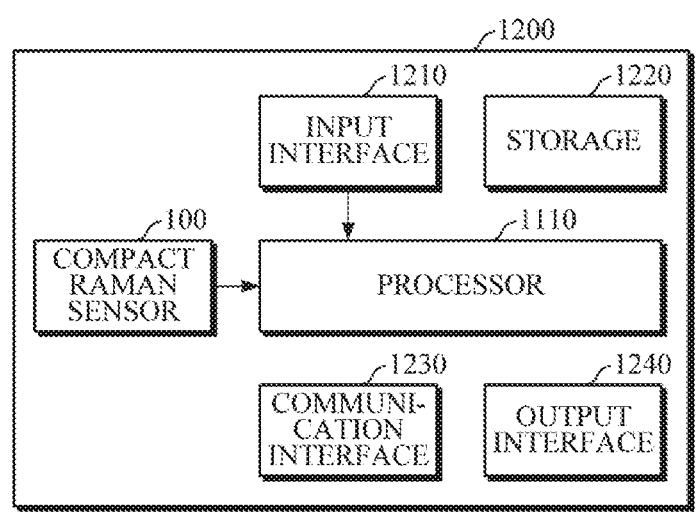
FIG. 12 is a diagram illustrating another example of an apparatus for estimating a bio-component according to an example embodiment.

FIG. 12 is a diagram illustrating another example of an apparatus for estimating a bio-component.

Referring to FIG. 12, the apparatus 1200 for estimating a bio-component includes the compact Raman sensor 100, the processor 1110, an input interface 1210, a storage 1220, a communication interface 1230, and an output interface 1240. The compact Raman sensor 100 and the processor 1110 are described above with reference to FIGS. 1 to 11, such that detailed description thereof will be omitted.

The input interface 1210 may receive input of various operation signals from a user. In one embodiment, the input interface 1210 may include a keypad, a dome switch, a touch pad (e.g., a static pressure touch pad, a capacitive touch pad, and the like), a jog wheel, a jog switch, a hardware (H/W) button, and the like. Particularly, the touch pad, which forms a layer structure with a display, may be referred to as a touch screen.

The storage 1220 may store programs or commands for operation of the apparatus 1200 for estimating a bio-component, and may store data input to and processed by the apparatus 1200 for estimating a bio-component. Further, the storage 1220 may store the two-dimensional Raman image of the skin and/or estimated bio-information, and the like.

The storage 1220 may include at least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the apparatus 1200 for estimating a bio-component may access an external storage medium, such as web storage and the like, which performs a storage function of the storage 1220 on the Internet.

The communication interface 1230 may communicate with an external device. For example, the communication interface 1230 may transmit data input by a user, the obtained two-dimensional Raman image data and/or bio-information to the external device, or may receive various data for obtaining two-dimensional Raman image data and/or estimating bio-information from the external device.

In this case, the external device may be medical equipment using the data input by a user, the obtained two-dimensional Raman image data and/or bio-information, a printer to print out results, or a display to display the results. In addition, the external device may be a digital television (TV), a desktop computer, a cellular phone, a smartphone, a tablet PC, a laptop computer, a personal digital assistant (PDA), a portable multimedia player (PMP), a navigation device, an MP3 player, a digital camera, a wearable device, and the like, but the external device is not limited thereto.

The communication interface 1230 may communicate with the external device by using Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, third generation (3G), fourth generation (4G), and fifth generation (5G) telecommunications, and the like. However, this is merely exemplary and not intended to be limiting.

The output interface 1240 may output the data input by a user, the obtained two-dimensional Raman image data and/or bio-information. In one embodiment, the output interface 1240 may output the data input by a user, the obtained two-dimensional Raman image data and/or bio-information by using at least one of an acoustic method, a visual method, and a tactile method. For example, the output interface 1240 may include a display, a speaker, a vibrator, and the like.

Figure 13:
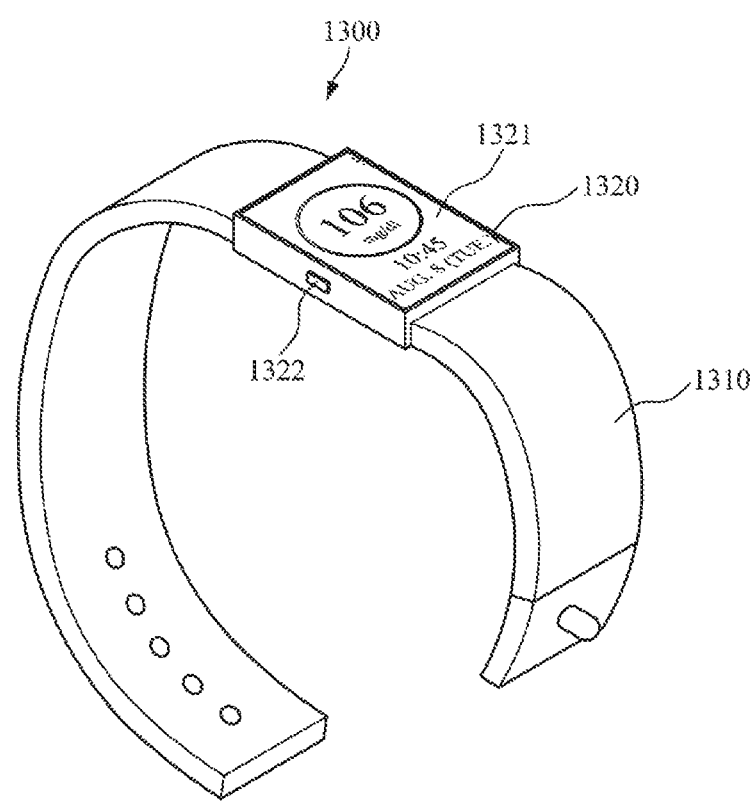
FIG. 13 is a diagram illustrating an example of a wrist-type wearable device according to an example embodiment.

FIG. 13 is a diagram illustrating an example of a wrist-type wearable device.

Referring to FIG. 13, the wrist-type wearable device 1300 includes a strap 1310 and a main body 1320.

The strap 1310 may be connected to both ends of the main body 1320 so as to be fastened in a detachable manner or may be integrally formed therewith as a smart band. The strap 1310 may be made of a flexible material to be wrapped around a user's wrist so that the main body 1320 may be worn on the wrist.

The main body 1320 may include the aforementioned apparatuses 1100 and 1200 for estimating a bio-component. Further, the main body 1320 may include a battery which supplies power to the apparatuses 1100 and 1200 for estimating a bio-component.

The compact Raman sensor 100 may be mounted at the bottom of the main body 1320 to be exposed to a user's wrist. Accordingly, when a user wears the wrist-type wearable device 1300, the compact Raman sensor 100 may naturally come into contact with the user's skin. In this case, the compact Raman sensor 100 may emit light onto the skin, and may collect and detect Raman scattered light from the skin.

The wrist-type wearable device 1300 may further include a display 1321 and an input interface 1322 which are mounted on the main body 1320. The display 1321 may display data processed by the apparatuses 1100 and 1200 for estimating a bio-component and/or the wrist-type wearable device 1300, processing result data thereof, and the like. The input interface 1322 may receive various operation signals from a user.

The embodiments of the present disclosure may be implemented by computer-readable code stored on a non-transitory computer-readable recording medium and executed by a processor. Code and code segments for implementing the embodiments of the present disclosure may be deduced by computer programmers of ordinary skill in the art. The non-transitory computer-readable medium may be any type of recording device in which data is stored in a computer-readable manner. Examples of the non-transitory computer-readable medium include a ROM, a RAM, a CD-ROM, a magnetic tape, a floppy disc, an optical disk, and the like. Further, the non-transitory computer-readable medium may be distributed over a plurality of computer systems connected to a network so that code is written thereto and executed therefrom in a decentralized manner.

The present disclosure has been described herein with regard to the various embodiments. However, it will be obvious to those skilled in the art that various changes and modifications can be made without departing from the scope of the present disclosure. Thus, it is clear that the above-described embodiments are illustrative in all aspects and are not intended to limit the present disclosure.

What is claimed is:

1. A Raman sensor comprising:
   a light source assembly having a plurality of light sources configured to emit light to a plurality of skin points of skin, each of the plurality of skin points having a predetermined separation distance from a light collection region of the skin from which Raman scattered light is collected;
   a light collector configured to collect the Raman scattered light from the light collection region of the skin; and
   a detector configured to detect the collected Raman scattered light,
   wherein the light source assembly comprises:
   a first reflection surface for reflecting the light, emitted by the plurality of light sources, in a predetermined direction;
   a second reflection surface for reflecting a first light beam, reflected by the first reflection surface, toward a first skin point having a first predetermined separation distance; and
   a third reflection surface for reflecting a second light beam, reflected by the first reflection surface, toward a second skin point having a second predetermined separation distance,
   wherein the second reflection surface and the third reflection surface are arranged in a concentric circle.

2. The Raman sensor of claim 1, wherein the light source assembly is configured to adjust a light intensity of each of the plurality of light sources to emit light within a maximum permissible exposure limit.

3. The Raman sensor of claim 1, wherein the predetermined separation distance has a value greater than a sampling volume of the skin.

4. The Raman sensor of claim 3, wherein a center of the sampling volume is located at a center of the light collector.

5. The Raman sensor of claim 1, wherein the predetermined separation distance indicates a distance between a center of the light collection region of the skin, from which the Raman scattered light is collected, and a skin point on which the light is incident.

6. The Raman sensor of claim 1, wherein the plurality of light sources are arranged on an outer periphery of the light collector in at least one of a linear shape, a circular shape, and a polygonal shape.

7. The Raman sensor of claim 1, wherein the predetermined direction is a direction toward a center of the light collector.

8. The Raman sensor of claim 1, wherein the first reflection surface and the second reflection surface are formed in a concentric ring.

9. The Raman sensor of claim 1, wherein the predetermined separation distance is configured to be adjusted by a reflection angle of the second reflection surface.

10. The Raman sensor of claim 9, wherein the light source assembly is configured to set all reflection angles of the second reflection surface to a same value, or adjust at least some of the reflection angles to a different value to set the predetermined separation distance to the same value for all of the plurality of skin points or to a different value for at least some of the plurality of skin points.

11. The Raman sensor of claim 1, wherein the light source assembly further comprises a filter for passing light of a specific wavelength, among the reflected light.

12. The Raman sensor of claim 1, wherein a radius of the second reflection surface and a radius of the third reflection surface are different from each other.

13. The Raman sensor of claim 1, wherein the predetermined separation distance is set based on at least one of a type of an analyte to be measured, a wavelength band, a light intensity, a shape of a device having the Raman sensor, a size of the device having the Raman sensor, and a computing performance of the device having the Raman sensor.

14. The Raman sensor of claim 1, wherein the light source assembly further comprises a filter for passing light of a specific wavelength, among the emitted light.

15. The Raman sensor of claim 1, wherein the plurality of light sources comprises a first light source configured to emit first light of a first wavelength, and a second light source configured to emit second light of a second wavelength.

16. The Raman sensor of claim 15, wherein the first light source and the second light source are arranged in a concentric circle, and have different radiuses.

17. The Raman sensor of claim 1, wherein the light source assembly further comprises a filter for passing light of a first specific wavelength among the reflected first light, and passing light of a second specific wavelength among the reflected second light.

18. The Raman sensor of claim 1, wherein the light collector comprises:
 a lens for collimating the Raman scattered light from the skin; and
 a filter for removing light of a specific wavelength from the collimated Raman scattered light.

19. The Raman sensor of claim 18, wherein the light collector further comprises a light collecting shield which is positioned in a light collection path between the skin and the lens, and that is configured to prevent light, other than the Raman scattered light, from being collected.

* * * * *